(12) United States Patent
Huchel et al.

(10) Patent No.: US 9,217,126 B2
(45) Date of Patent: Dec. 22, 2015

(54) PHOTOLABILE FRAGRANCE STORAGE SUBSTANCES

(75) Inventors: Ursula Huchel, Cologne (DE); Christian Kropf, Hilden (DE); Axel Griesbeck, Cologne (DE); Olga Hinze, Cologne (DE); Uta Sundermeier, Cologne (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 167 days.

(21) Appl. No.: 13/156,537

(22) Filed: Jun. 9, 2011

(65) Prior Publication Data

US 2011/0237685 A1 Sep. 29, 2011

Related U.S. Application Data

(63) Continuation of application No. PCT/EP2009/063145, filed on Oct. 9, 2009.

(30) Foreign Application Priority Data

Dec. 9, 2008 (DE) .......................... 10 2008 060 886

(51) Int. Cl.
| | |
|---|---|
| A61K 47/00 | (2006.01) |
| C11D 3/50 | (2006.01) |
| A61K 8/35 | (2006.01) |
| A61Q 13/00 | (2006.01) |
| C07C 49/82 | (2006.01) |
| C07C 49/83 | (2006.01) |
| C11B 9/00 | (2006.01) |
| A61Q 19/00 | (2006.01) |

(52) U.S. Cl.
CPC . *C11D 3/507* (2013.01); *A61K 8/35* (2013.01); *A61Q 13/00* (2013.01); *C07C 49/82* (2013.01); *C07C 49/83* (2013.01); *C11B 9/0061* (2013.01); *A61Q 19/00* (2013.01); *C07B 2200/07* (2013.01); *C07C 2102/42* (2013.01)

(58) Field of Classification Search
None
See application file for complete search history.

(56) References Cited

U.S. PATENT DOCUMENTS

| | | | |
|---|---|---|---|
| 6,723,688 B1 * | 4/2004 | Malik et al. | ................... 510/130 |
| 6,949,680 B2 | 9/2005 | Herrmann | |
| 2002/0077508 A1 | 6/2002 | Gautschi et al. | |
| 2002/0094938 A1 | 7/2002 | Dykstra et al. | |
| 2003/0129212 A1 | 7/2003 | Herrmann | |
| 2004/0067870 A1* | 4/2004 | Miracle | .......................... 512/10 |

FOREIGN PATENT DOCUMENTS

| | | |
|---|---|---|
| WO | WO2005/051336 A1 | 6/2005 |
| WO | WO2007/087977 A1 | 8/2007 |
| WO | WO 2007/121845 * 11/2007 | ............. A61Q 19/02 |

OTHER PUBLICATIONS

Ooi et al (Tetrahedron Lett 40:2133-2136, 1999).*
Tian et al (Tetrahedron Lett 42:1803-1805, 2001).*
PCT International Search Report (PCT/EP2009/063145) dated Nov. 6, 2010.
Abate et al, J. Org. Chem. 2005, 70, pp. 1281-1290.
Tanabe et al, Tetrahedron 58 (2002), pp. 8269-8280.
Arctander, Perfume and Flavor Chemicals vol. I, monographs No. 1 to 1790 (A-J).
Arctander, Perfume and Flavor Chemicals vol. II: monographs No. 1791 to 3102 (K-Z).
Hasegawa et al, Tetrahedron Letters vol. 37, No. 39 (1996), pp. 7079-7082.
DIN5035-6, Artificial lighting—Part 6: Measurement and Evaluation, Nov. 2006, pp. 1-34.

* cited by examiner

*Primary Examiner* — Craig Ricci
(74) *Attorney, Agent, or Firm* — Thomas G. Krivulka

(57) ABSTRACT

Photolabile fragrance storage substances capable of photoinduced release of odorant aldehydes and odorant ketones are described in addition to a process for long-lasting fragrancing of surfaces and a process for producing said fragrance storage substances.

1 Claim, No Drawings

PHOTOLABILE FRAGRANCE STORAGE SUBSTANCES

CROSS-REFERENCE TO RELATED APPLICATIONS

This application is a continuation of PCT Application Serial No. PCT/EP2009/063145, filed on Oct. 9, 2009, which claims priority under 35 U.S.C. §119 to 10 2008 060 886.6 (DE), filed on Dec. 9, 2008. The disclosures PCT/EP2009/063145 and DE 10 2008 060 886.6 are hereby incorporated by reference in their entirety.

FIELD OF THE INVENTION

The present invention relates to compositions comprising at least one certain β-hydroxy ketone, which is capable of releasing a carbonyl compound in particular on exposure to electromagnetic radiation, preferably an odorant aldehyde or an odorant ketone. Furthermore, it relates to a method for releasing odorant aldehydes and/or odorant ketones from certain β-hydroxy ketones. It also relates to a method for long-lasting fragrancing of surfaces. It relates to the use of certain β-hydroxy ketones as scent precursors in washing and cleaning agents, in cosmetic agents and in air fresheners.

BACKGROUND OF THE INVENTION

Textile and surface treatment agents and/or cosmetic agents mostly contain fragrance substances (odorant substances) which impart a pleasant and fresh odor to the agents. The terms odorant substances and fragrance substances are used synonymously in this invention. The fragrance substances usually mask the inherent fragrance note of the other ingredients so that the user has a positive odor impression. Fragrance substances are especially important ingredients of the composition in the field of washing agents because laundry should have a fresh and pleasant fragrance when damp as well as when dry. There is a fundamental problem in the use of fragrance substances in that these are volatile substances; otherwise no fragrance effect could be achieved. However, one strives to achieve the most uniform and long-lasting fragrance effect possible. For example, it is known that the fragrance impression of a perfume changes over a period of time because the odorant substances, which represent the fresh and light notes of the perfume, evaporate more quickly due to their high vapor pressure than the fragrance substances representing heart notes and base notes.

One approach toward solving this problem, namely achieving the most uniform and long-lasting fragrance effect, consists of applying fragrance substances to carrier materials and coating the fragranced carriers or encapsulating fragrance substances or incorporating them into compounds (for example, cyclodextrin perfume complexes). In addition, there is the option of chemically binding the fragrance substances to carrier media, so that the chemical bond is cleaved slowly, thereby releasing the fragrance substance. Such a carrier-bound precursor of a fragrance substance is also referred to as a "pro-fragrance" or a fragrance storage substance. In this context, International Patent Application WO 2007/087977 discloses the use of 1-aza-3,7-dioxabicyclo [3.3.0]octane compounds as fragrance storage substances for delayed release of fragrance aldehydes and fragrance ketones by hydrolysis. An alternative option for delayed release of fragrance substances is to use so-called photoactivatable substances as fragrance storage substances. Breaking of a covalent bond in the molecule of the fragrance storage substance is induced by exposure to sunlight or some other electromagnetic radiation source of a certain wavelength, thereby releasing the fragrance substance. The process described here must tolerate the presence of oxygen and water for effective release of the fragrance substance.

In this context, U.S. Pat. No. 6,949,680 discloses the use of certain phenyl or pyridyl ketones as photoactivatable substances, which release a terminal alkene as an active substance in the presence of light in a photochemical fragmentation. The aforementioned active substance has a fragrancing or antimicrobial activity, for example, which is delayed by the photochemically induced decomposition and is released over a rather long period of time on a certain surface. The aforementioned photolabile phenyl or pyridyl ketones are produced as fragrance storage substances in a complex multistep synthesis process using protective group orientations, wherein the synthesis must be adapted individually for each individual active substance.

In spite of the advances in the prior art, there is an ongoing need to enable a delayed release of fragrance aldehyde (odorant aldehydes) and fragrance ketones (odorant ketones).

SUMMARY OF THE INVENTION

It has now surprisingly been found that a composition comprising certain β-hydroxy ketones described below allows the delayed release of fragrance aldehydes (odorant aldehydes) or fragrance ketones (odorant ketones).

The subject matter of the present invention is a composition containing at least one β-hydroxy ketone of general formula (I):

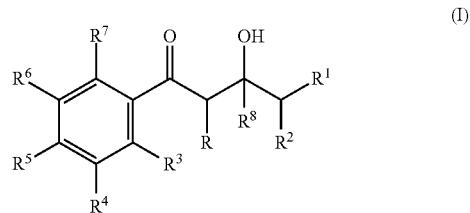

wherein in this formula, independently of one another, R and R8 stand for a hydrogen atom or an organic radical, in particular for a linear or branched, substituted or unsubstituted alkyl or alkylene group of $C_1$ to $C_{20}$, but preferably for a methyl radical, and wherein, independently of one another, R1 and R2 stand for a hydrogen atom or for organic radicals such as in particular a linear or branched, substituted or unsubstituted alkyl or alkylene group of $C_1$ to $C_{20}$ preferably $C_4$ to $C_{20}$, wherein the R1 and R2 radicals together may also form a ring system in particular a substituted or unsubstituted mono- or polycycloalkyl group of $C_3$ to $C_8$ or a substituted or unsubstituted phenyl group, and wherein, independently of one another, R3, R4, R5, R6 and R7 stand for hydrogen, a halogen atom, $NO_2$, a linear or branched, substituted or unsubstituted alkoxy group with 1 to 15 carbon atoms or a linear or branched, substituted or unsubstituted alkyl group with 1 to 15 carbon atoms.

The invention also makes it possible to lengthen the fragrance effect of other fragrance substances which are also present in the composition. It also makes it possible to achieve a long-lasting fresh odor. It enables long-lasting fragrancing of surfaces. It enables a controllable photoinduced release of odorant aldehydes and odorant ketones.

DETAILED DESCRIPTION OF THE INVENTION

According to the invention, preferred compositions contain at least one β-hydroxy ketone of general formula (II) and/or of general formula (III):

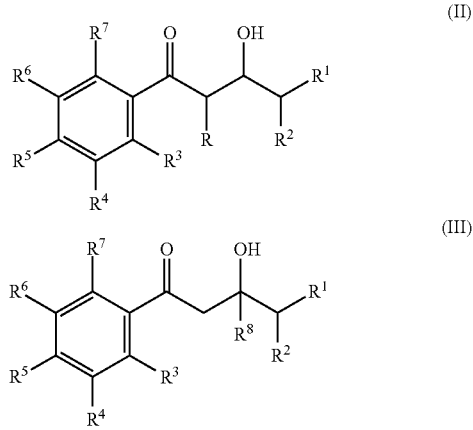

wherein in these formulas (II) and (III), independently of one another, the radicals R, R1, R2, R3, R4, R5, R6, R7, R8 are defined as indicated above in conjunction with formula (I). It is preferred, based on formula (II), if the R radical stands for a linear or branched, substituted or unsubstituted alkyl or alkylene group of $C_1$ to $C_{20}$ but preferably for a methyl radical. Based on formula (III), it is preferred if the R8 radical stands for a linear or branched, substituted or unsubstituted alkyl or alkylene group of $C_1$ to $C_{20}$, but preferably for a methyl radical. Formulas (II) and (III) form simple subsets of formula (I).

In addition, a compound of general formula (I) according to the invention, wherein four of the five aryl substituents R3, R4, R5, R6 and R7 stand for hydrogen is preferred. Preferably R3, R4, R6 and R7 stand for hydrogen while the substituent in para position R5 preferably stands for a halogen atom, $NO_2$, a linear or branched, substituted or unsubstituted alkoxy group with 1 to 15 carbon atoms or a linear or branched, substituted or unsubstituted alkyl group with 1 to 15 carbon atoms. In an especially preferred embodiment of the invention, R5 stands for Cl, Br, $NO_2$ or an alkyl or alkoxy group comprising 1 to 4 carbon atoms. The linear or branched, substituted or unsubstituted alkyl group is preferably a methyl or ethyl group and/or the linear or branched, substituted or unsubstituted alkoxy group is a methoxy, ethoxy, isopropoxy or tert-butoxy group. A substitution in para position (R5) is especially preferred because the electronic structure of the aromatic ring can be modified most effectively here, so that the absorption maximum of compounds of general formula (I) can easily be adapted to a certain wavelength. A compound according to the invention of general formula (II), wherein all five aryl substituents R3, R4, R5, R6 and R7 stand for hydrogen is also preferred. What was said above with regard to the general formula (I) and the five aryl substituents R3, R4, R5, R6 and R7 naturally also applies to general formulas (II) and (III).

On exposure to electromagnetic radiation, in particular comprising the wavelengths of 200 to 400 nm, the aforementioned β-hydroxy ketone of general formula (I) can according to the invention release a preferably fragrant carbonyl compound, i.e., a fragrance ketone or fragrance aldehyde. Natural sunlight may preferably serve as the electromagnetic radiation in the sense of the present invention. This is naturally also true of the β-hydroxy ketones of general formulas (II) and (III).

In a preferred embodiment of the invention, a composition according to the invention is characterized in that the β-hydroxy ketone releases a carbonyl compound of formula (IV) and a carbonyl compound of formula (V) on exposure to electromagnetic radiation comprising the wavelengths of 200 to 400 nm, wherein the radicals R, R1, R2, R3, R4, R5, R6, R7, R8 are defined as indicated above in conjunction with formula (I):

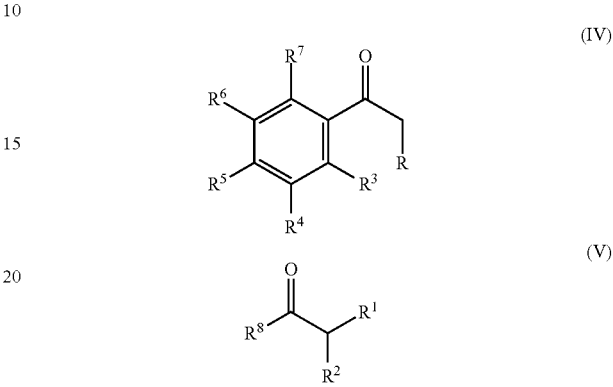

It is preferable if the radical R in formula (IV) stands for a hydrogen atom or a methyl radical. It is also preferable if in formula (V) the radical R8 stands for a hydrogen atom or a methyl radical.

The present invention thus enables the targeted release of pleasant odorant aldehydes and ketones by exposure to electromagnetic radiation, in particular comprising the wavelengths of 200 to 400 nm.

In a preferred embodiment of the invention, at least one odorant aldehyde is released on exposure to electromagnetic radiation comprising wavelengths of 200 to 400 nm, the odorant aldehyde preferably being selected from the group comprising melonal, triplal, ligustral, adoxal, anisaldehyde, cymal, ethyl vanillin, Florhydral, helional, heliotropin, hydroxycitronellal, Koavone, laurinaldehyde, lyral, methyl nonyl acetaldehyde, p,t-bucinal, phenylacetaldehyde, undecylene aldehyde, vanillin, 2,6,10-trimethyl-9-undecenal, 3-dodecen-1-al, α-n-amylcinnamaldehyde, 4-methoxybenzaldehyde, benzaldehyde, 3-(4-tert-butylphenyl)propanal, 2-methyl-3-(para-methoxyphenylpropanal), 2-methyl-4-(2,6,6-trimethyl-2(1)-cyclohexen-1-yl)butanal, 3-phenyl-2-propenal, cis-/trans-3,7-dimethyl-2,6-octadien-1-al, 3,7-dimethyl-6-octen-1-al, [(3,7-dimethyl-6-octenyl)oxy]acetaldehyde, 4-isopropylbenzyl aldehyde, 1,2,3,4,5,6,7,8-octahydro-8,8-dimethyl-2-naphthaldehyde, 2,4-di-methyl-3-cyclohexene-1-carboxyaldehyde, 2-methyl-3-(isopropylphenyl)propanal, decyl aldehyde, 2,6-dimethyl-5-heptenal, 4-(tricyclo[5.2.1.0(2,6)]-decylidene-8)butanal, octahydro-J-methano-1H-indene carboxaldehyde, 3-ethoxy-4-hydroxybenzaldehyde, para-ethyl-α,α-dimethylhydrocinnamaldehyde, α-methyl-3,4-(methylenedioxy)hydro-cinnamaldehyde, 3,4-methylenedioxybenzaldehyde, α-n-hexylcinnamaldehyde, m-cymene-7-carboxaldehyde, α-methylphenylacetaldehyde, 7-hydroxy-3,7-dimethyloctanal, undecenal, 2,4,6-trimethyl-3-cyclohexene-1-carboxaldehyde, 4-(3)(4-methyl-3-pentenyl)-3-cyclohexene carboxaldehyde, 1-dodecanal, 2,4-dimethylcyclohexene-S-carboxaldehyde, 4-(4-hydroxy-4-methylphenyl-S-cyclohexene-1-carboxaldehyde, 7-methoxy-3,7-dimethyloctan-1-al, 2-methylundecanal, 2-methyldecanal, 1-nonanal, 1-octanal, 2,6,10-trimethyl-5,9-undecadienal, 2-methyl-3-(4-tert-butyl)propanol, dihydrocinnamaldehyde, 1-methyl-4-(4-methyl-3-pentenyl)-3-cyclohexene-1-carboxaldehyde, 5- or 6-methoxyhexahydro-4,7-methanoindane-1- or -2-carboxyaldehyde, 3,7-dimethyloctan-1-al, 1-undecanal, 10-undecen-1-al, 4-hydroxy-3-methoxybenzaldehyde, 1-methyl-3-(4-methylpentyl)-3-cyclohexene carboxyaldehyde, 7-hydroxy-3,7-dimethyloctanal, trans-4-decenal, 2,6-nonadienal, para-tolylacetaldehyde, 4-methylphenylacetaldehyde, 2-methyl-4-(2,6,6-trimethyl-1-cyclohexen-1-yl)-2-butenal, ortho-methoxycinnamaldehyde, S,S,δ-trimethyl-S-cyclohexene carboxaldehyde, 3,7-dimethyl-2-methylene-6-octenal, phenoxyacetaldehyde, 5,9-dimethyl-4,8-decadienal, peony aldehyde (6,10-dimethyl-3-oxa-5,9-undecadien-1-al), hexahydro-4,7-methanoindane-1-carboxalde-hyde, 2-methyloctanal, α-methyl-4-(1-methylethyl) benzene acetaldehyde, 6,6-dimethyl-2-norpinene-2-propionaldehyde, para-methylphenoxyacetaldehyde, 2-methyl-3-phenyl-2-propen-1-al, 3,5,5-trimethylhexanal, hexahydro-8,8-dimethyl-2-naphthaldehyde, 3-propyl-bicyclo[2.2.1]hept-5-ene-2-carbaldehyde, 9-decenal, 3-methyl-5-phenyl-1-pentanal, methyl nonyl acetaldehyde, 1-p-menthene-q-carboxaldehyde, citral, lilial, 1-decanal, Florhydral as well as 2,4-dimethyl-3-cyclohexene-1-carboxaldehyde or mixtures of these.

Likewise, another preferred embodiment of the invention is when, on exposure to electromagnetic radiation comprising the wavelengths of 200 to 400 nm, at least one odorant ketone is released, preferably selected from the group comprising buccoxime, isojasmone, methyl β-naphthyl ketone, musk indanone, tonalide/musk plus, α-damascone, β-damascone, δ-damascone, isodamascone, damascenone, damarose, methyl dihydrojasmonate, menthone, carvone, camphor, fenchone, α-ionene, β-ionone, dihydro-β-ionone, γ-methyl so-called ionone, fleuramone, dihydrojasmone, cis-jasmone, iso-E-super, methyl cedrenyl ketone or methyl cedrylone, acetophenone, methyl acetophenone, para-methoxyacetophenone, methyl β-naphtyl ketone, benzyl acetone, benzophenone, para-hydroxyphenylbutanone, celery ketone or livescone, 6-isopropyldecahydro-2-naphthone, dimethyloctenone, freskomenth, 4-(1-ethoxyvinyl)-3,3,5,5-tetramethylcyclohexanone, methyl heptenone, 2-(2-(4-methyl-3-cyclohexene-1-yl)propyl)cyclopentanone, 1-(p-menthen-6 (2)-yl)-1-propanone, 4-(4-hydroxy-3-methoxyphenyl)-2-butanone, 2-acetyl-3,3-dimethylnorbornane, 6,7-dihydro-1,1,2,3,3-pentamethyl-4(5H)-indanone, 4-damascol, dulcinyl or cassion, gelson, hexalon, isocyclemone E, methyl cyclocitron, methyl lavendel ketone, orivon, para-tert-butylcyclohexanone, verdone, delphon, muscone, neobutenone, plicatone, veloutone, 2,4,4,7-tetramethyloct-6-en-3-one, tetrameran as well as hedione.

The odorant aldehydes and odorant ketones that can be released according to the invention may have an aliphatic, cycloaliphatic, aromatic, ethylenically unsaturated structure or a combination of these structures. Furthermore, additional heteroatoms or polycyclic structures may also be present. These structures may have suitable substituents such as hydroxyl groups or amino groups.

Another preferred embodiment of the invention is when at least one of the following β-hydroxy ketones according to formulas (VI) or (VII) is present:

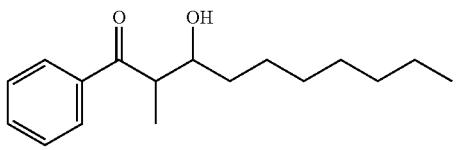

(VI)

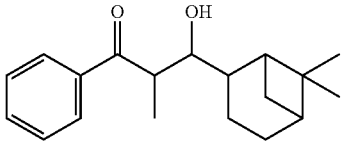

(VII)

The composition according to the invention preferably contains β-hydroxy ketones of general formula (I) in amounts between 0.0001 and 95 wt %, based on the total composition. A possible upper limit for the β-hydroxy ketones according to the invention in the composition may also be, for example, 80 wt %, 70 wt %, 60 wt %, 50 wt %, 40 wt %, 30 wt %, 20 wt %, 10 wt % or, for example, even 5 wt %, based on the total composition. A possible lower limit for the β-hydroxy ketones according to the invention in the composition may also be, for example, 0.001 wt %, 0.01 wt %, 0.1 wt % or, for example, 0.5 wt %, based on the total composition.

The composition according to the invention may also comprise, in addition to the β-hydroxy ketones according to the invention, other ingredients, e.g., solvents, carrier materials, additional fragrance substances, colorant substances, surfactants, etc. The type and quantity of additional ingredients included is uncritical in principle and depends primarily on the intended purpose of the composition according to the invention. If the composition according to the invention is a washing agent, for example, it will logically also contain the conventional ingredients for washing agents, e.g., surfactants, builders, etc.

In a preferred embodiment of the invention, the composition according to the invention contains at least one additional fragrance substance. The term "additional fragrance substance" thus refers to substances other than the β-hydroxy ketones of general formula (I) included according to the invention, which may have a different fragrance effect.

The preferred fragrance substances and/or perfume oils that may be used in addition are not subject to any restrictions. Thus in particular synthetic or natural odorant substance compounds of the types of esters, ethers, aldehydes (fragrance aldehydes, odorant aldehydes), ketones (fragrance ketones, odorant ketones), alcohols, hydrocarbons, acids, carbonic acid esters, aromatic hydrocarbons, aliphatic hydrocarbons, saturated and/or unsaturated hydrocarbons and mixtures of these may be used as fragrance substances.

As fragrance aldehydes or fragrance ketones, all the conventional fragrance aldehydes and fragrance ketones may be used which are typically used to induce a pleasant fragrance perception. Suitable fragrance aldehydes and fragrance ketones are familiar to those skilled in the art. The fragrance ketones may comprise all ketones which are able to impart a desired fragrance or a fresh perception, for example, those already mentioned in the description. Mixtures of different ketones may also be used. The ketones may preferably be selected from α-damascone, δ-damascone, isodamascone, carvone, γ-methylionone, iso-E-super, 2,4,4,7-tetramethyloct-6-en-3-one, benzyl acetone, β-damascone, damascenone, methyl dihydrojasmonate, methyl cedrylone, hedione and mixtures of these.

Suitable fragrance aldehydes may be any aldehydes which impart a desired fragrance or fresh perception according to the fragrance ketones. These may in turn be individual aldehydes or aldehyde mixtures. Suitable aldehydes include, for example, the aldehydes already mentioned in the preceding text.

The fragrance aldehydes and fragrance ketones may have an aliphatic, cycloaliphatic, aromatic, ethylenically unsaturated structure or a combination of these structures. Furthermore, there may be additional heteroatoms or polycyclic structures. These structures may have suitable substituents such as hydroxyl groups or amino groups.

For further suitable fragrance substances selected from aldehydes and ketones, reference is made to Steffen Arctander published 1960 and 1969, respectively, reprinted 2000 ISBN: Aroma Chemicals, vol. 1: 0-931710-37-5, Aroma Chemicals, vol. 2: 0-931710-38-3.

Suitable fragrance substances of the ester type include, for example, benzyl acetate, phenoxyethyl isobutyrate, p-tert-butylcyclohexyl acetate, linalyl acetate, dimethylbenzylcarbinyl acetate (DMBCA), phenylethyl acetate, benzyl acetate, ethylmethylphenyl glycinate, allylcyclohexyl propionate, styrallyl propionate, benzyl salicylate, cyclohexyl salicylate, floramate, melusate and jasmacyclate. Odorant substance compounds of the hydrocarbon type include, for example, terpenes such as limonene and pinene.

Suitable fragrance substances of the ether type include, for example, benzylethyl ether and ambroxan. Suitable fragrance substance alcohol include, for example, 10-undecen-1-ol, 2,6-dimethylheptan-2-ol, 2-methylbutanol, 2-methylpentanol, 2-phenoxyethanol, 2-phenylpropanol, 2-tert-butylcyclohexanol, 3,5,5-trimethylcyclohexanol, 3-hexanol, 3-methyl-5-phenylpentanol, 3-octanol, 1-octen-3-ol, 3-phenylpropanol, 4-heptenol, 4-isopropylcyclohexanol, 4-tert-butylcyclohexanol, 6,8-dimethyl-2-nonanol, 6-nonen-1-ol, 9-decen-1-ol, α-methylbenzyl alcohol, α-terpineol, amyl salicylate, benzyl alcohol, benzyl salicylate, β-terpineol, butyl salicylate, citronellol, cyclohexyl salicylate, decanol, dihydromyrcenol, dimethylbenzylcarbinol, dimethylheptanol, dimethyloctanol, ethyl salicylate, ethyl vanillin, anethol, eugenol, geraniol, heptanol, hexyl salicylate, isoborneol, isoeugenol, isopulegol, linalool, menthol, myrtenol, n-hexanol, nerol, nonanol, octanol, para-menthan-7-ol, phenylethyl alcohol, phenol, phenyl salicylate, tetrahydrogeraniol, tetrahydrolinalool, thymol, trans-2-cis-6-nonadienol, trans-2-nonen-1-ol, trans-2-octenol, undecanol, vanillin, cinnamic alcohol, wherein when multiple fragrance substance alcohols are present, they may be selected independently of one another.

Fragrance substances and/or perfume oils may also be natural odorant mixtures such as those accessible from plant sources, e.g., pine, citrus, jasmine, patchouli, rose or ylang-ylang oil. Also suitable are muscat, sage oil, chamomile oil, clove oil, mint oil, cinnamon leaf oil, lime blossom oil, juniper berry oil, vetiver oil, olibanum [frankincense] oil, galbanum oil and labdanlum oil as well as orange blossom oil, neroli oil, orange peel oil and sandalwood oil. The fragrance substances and/or perfume oils may also be essential oils, for example, angelica root oil, anise oil, arnica blossom oil, basal oil, bay oil, champaca blossom oil, silver fir oil, silver fir cone oil, elemi oil, eucalyptus oil, fennel oil, spruce needle oil, galbanum oil, geranium oil, gingergrass oil, guaiac wood oil, gurjun balsam oil, helichrysum oil, ho leaf oil, ginger oil, iris oil, cajeput oil, calmus oil, chamomile oil, camphor oil, canaga oil, cardamom oil, cassia oil, pine needle oil, copaiva balsam oil, coriander oil, spearmint oil, caraway oil, cumen oil, lavender oil, lemongrass oil, lime oil, mandarin oil, lemon balm oil, musk seed oil, myrrh oil, clove oil, neroli oil, niaouli oil, olibanum oil, origanum oil, palmarosa oil, patchouli oil, peru balsam oil, petit grain oil, pepper oil, peppermint oil, pimento oil, pine oil, rose oil, rosemary oil, sandalwood oil, celery oil, spike oil, stemanis oil, turpentine oil, thuja oil, thyme oil, verbena oil, vetiver oil, juniper berry oil, vermouth oil, wintergreen oil, ylang-ylang oil, ysop oil, cinnamon oil, cinnamon leaf oil, citronella oil, lemon oil and cypress oil.

The total quantity of additional fragrance substances that may be used in the composition according to the invention preferably amounts to between 0.01 and 5 wt %, especially preferably between 0.1 and 3 wt % and most especially preferably between 0.5 and 2 wt % based on the total quantity of the composition. Mixtures of different fragrance substances (from the various classes of fragrance substances listed above) are preferred for use when they create an appealing fragrance note when used together.

In another preferred embodiment of the invention, the composition according to the invention is a washing or cleaning agent, a cosmetic preparation or an air freshener.

The washing or cleaning agents may be in particular a textile treatment agent in the form of a textile washing agent, a fabric softener, softener washing agent or washing additive. Likewise they may be, for example, cleaning agents for hard surfaces, preferably a dishwashing agent, in particular a machine dishwashing agent. Likewise they may be cleaning agents, e.g., household cleaners, all-purpose cleaners, window cleaners, floor cleaners, etc.

The β-hydroxy ketone according to the invention of general formula (I) is preferably present in the composition according to the invention, in particular in the form of a washing agent, fabric softener, fabric softening washing agent or washing additive in amounts of preferably between 0.01 and 5 wt %, especially preferably between 0.1 and 3 wt % and most especially preferably between 0.5 and 2 wt %, each based on the total amount of the composition. The composition according to the invention such as in particular washing or cleaning agents may be solid or liquid, but liquid agents, preferably liquid washing or cleaning agents may be preferred.

In particular for the case when the agent according to the invention is a washing or cleaning agent, it is preferable for it to contain at least one surfactant selected from the group consisting of anionic, nonionic, zwitterionic and amphoteric surfactants.

For the case when the agent according to the invention is a fabric softening agent ("2 in 1"), it is preferable for it to contain a fabric softening component as well as at least one surfactant selected from a group consisting of anionic, nonionic, zwitterionic and amphoteric surfactants.

Washing additives are used on spots or heavy soiling for targeted pretreatment of laundry before washing. Washing additives include, for example, pretreatment agents, presoaking agents, decolorizers and stain remover salt.

For the case when the agent according to the invention is a fabric softener, it is preferable for it to contain a fabric softening component.

Fabric softeners are preferred as agents according to the invention because they come in contact with the textiles only in the last step of a conventional textile washing operation, the rinse cycle and thus a particularly large quantity of the fragrance substances may be absorbed onto the textile without any risk of the fragrance substances being removed again in subsequent steps.

Another subject matter of the present invention is a method for the release of carbonyl compounds, preferably odorant aldehydes and/or odorant ketones of formula (V), from β-hydroxy ketones of general formula (I):

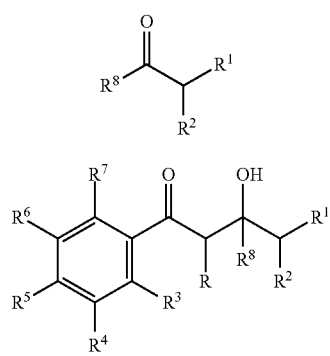

by using electromagnetic radiation comprising the wavelengths from 200 to 400 nm, wherein the radicals R, R1, R2, R3, R4, R5, R6, R7, R8 are in turn defined as already indicated above, in particular for applications in conjunction with the use of washing or cleaning agents, cosmetics as well as air fresheners In a preferred embodiment of the method, it serves to release odorant aldehydes, in particular those selected from the group comprising melonal, triplal, ligustral, adoxal, anisaldehyde, cymal, ethyl vanillin, Florhydral, helional, heliotropin, hydroxycitronellal, Koavone, laurinaldehyde, lyral, methyl nonyl acetaldehyde, p,t-bucinal, phenylacetaldehyde, undecylene aldehyde, vanillin, 2,6,10-trimethyl-9-undecenal, 3-dodecen-1-al, α-n-amyl-cinnamaldehyde, 4-methoxybenzaldehyde, benzaldehyde, 3-(4-tert-butylphenyl)propanal, 2-methyl-3-(para-methoxyphenylpropanal), 2-methyl-4-(2,6,6-trimethyl-2(1)-cyclohexen-1-yl)butanal, 3-phenyl-2-propenal, cis-/trans-3,7-dimethyl-2,6-octadien-1-al, 3,7-dimethyl-6--octen-1-al, [(3,7-dimethyl-6-octenyl) oxy]acetaldehyde, 4-isopropylbenzyl aldehyde, 1,2,3,4,5,6, 7,8-octahydro-8,8-dimethyl-2-naphthaldehyde, 2,4-dimethyl-3-cyclohexene-1-carboxyaldehyde, 2-methyl-3-(isopropylphenyl)propanal, decyl aldehyde, 2,6-dimethyl-5-heptenal, 4-(tricyclo[5.2.1.0(2,6)]-decylidene-8)butanal, octahydro-J-methano-1H-indene carboxaldehyde, 3-ethoxy-4-hydroxybenzaldehyde, para-ethyl-α,α-dimethylhydrocinnam-aldehyde, α-methyl-3,4-(methylenedioxy)hydrocinnamaldehyde, 3,4-methylene-dioxybenzaldehyde, α-n-hexylcinnamaldehyde, m-cymene-7-carboxaldehyde, α-methylphenylacetaldehyde, 7-hydroxy-3,7-dimethyloctanal, undecenal, 2,4,6-trimethyl-3-cyclohexene-1-carboxaldehyde, 4-(3)(4-methyl-3-pentenyl)-3-cyclohexene carboxaldehyde, 1-dodecanal, 2,4-dimethylcyclohexene-S-carboxaldehyde, 4-(4-hydroxy-4-methylphenyl-S-cyclohexene-1-carboxaldehyde, 7-methoxy-3,7-dimethyloctan-1-al, 2-methylundecanal, 2-methyldecanal, 1-nonanal, 1-octanal, 2,6,10-trimethyl-5,9-undecadienal, 2-methyl-3-(4-tert-butyl)propanol, dihydrocinnamaldehyde, 1-methyl-4-(4-methyl-3-pentenyl)-3-cyclohexene-1-carboxaldehyde, 5- or 6-methoxyhexahydro-4,7-methanoindane-1- or -2-carboxyaldehyde, 3,7-dimethyloctan-1-al, 1-undecanal, 10-undecen-1-al, 4-hydroxy-3-methoxybenzaldehyde, 1-methyl-4-(4-methylpentyl)-3-cyclohexene carboxyaldehyde, 7-hydroxy-3,7-dimethyloctanal, trans-4-decenal, 2,6-nonadienal, para-tolylacetaldehyde, 4-methylphenylacetaldehyde, 2-methyl-4-(2,6,6-trimethyl-1-cyclohexen-1-yl)-2-butenal, ortho-methoxycinnamaldehyde, S,S,δ-trimethyl-S-cyclohexene carboxaldehyde, 3,7-dimethyl-2-methylene-6-octenal, phenoxyacetaldehyde, 5,9-dimethyl-4,8-decadienal, peony aldehyde (6,10-dimethyl-3-oxa-5,9-undecadien-1-al), hexahydro-4,7-methanoindane-1-carboxaldehyde, 2-methyloctanal, α-methyl-4-(1-methylethyl)benzene acetaldehyde, 6,6-dimethyl-2-norpinene-2-propionaldehyde, para-methylphenoxyacetaldehyde, 2-methyl-3-phenyl-2-propen-1-al, 3,5,5-trimethylhexanal, hexahydro-8,8-dimethyl-2-naphthaldehyde, 3-propylbicyclo[2.2.1]hept-5-ene-2-carbaldehyde, 9-decenal, 3-methyl-5-phenyl-1-pentanal, methyl nonyl acetaldehyde, 1-p-menthene-q-carboxaldehyde, citral, lilial, 1-decanal, Florhydral[sic] as well as 2,4-dimethyl-3-cyclohexene-1-carboxaldehyde.

In a preferred embodiment of the method, it serves to release odorant ketones in particular selected from the group comprising selected from the group comprising buccoxime, isojasmone, methyl β-naphthyl ketone, musk indanone, tonalide/musk plus, α-damascone, β-damascone, δ-damascone, isodamascone, damascenone, damarose, methyl dihydrojasmonate, menthone, carvone, camphor, fenchone, α-ionene, β-ionone, dihydro-β-ionone, γ-methyl so-called ionone, fleuramone, dihydrojasmone, cis-jasmone, iso-E-super, methyl cedrenyl ketone or methyl cedrylone, acetophenone, methyl acetophenone, para-methoxyacetophenone, methyl β-naphtyl ketone, benzyl acetone, benzophenone, para-hydroxyphenylbutanone, celery ketone or livescone, 6-isopropyldecahydro-2-naphthone, dimethyloctenone, freskomenth, 4-(1-ethoxyvinyl)-3,3,5,5-tetramethylcyclohexanone, methyl heptenone, 2-(2-(4-methyl-3-cyclohexene-1-yl)propyl)cyclopentanone, 1-(p-menthen-6(2)-yl)-1-propanone, 4-(4-hydroxy-3-methoxyphenyl)-2-butanone, 2-acetyl-3,3-dimethyl-norbornane, 6,7-dihydro-1,1,2,3,3-pentamethyl-4(5H)-indanone, 4-damascol, dulcinyl or cassion, gelson, hexalon, isocyclemone E, methyl cyclocitron, methyl lavendel ketone, orivon, para-tert-butylcyclohexanone, verdone, delphon, muscone, neobutenone, plicatone, veloutone, 2,4,4,7-tetramethyloct-6-en-3-one, tetrameran as well as hedione.

Another subject matter of the invention is a method for long-lasting fragrancing of surfaces, wherein a composition according to the invention is applied to a surface to be fragranced and the aforementioned surface is then exposed to an electromagnetic radiation comprising the wavelengths from 200 to 400 nm. When the composition is a washing or cleaning agent and the surfaces to be fragranced are textile substrates or hard surfaces, this is a preferred embodiment of the invention.

Another subject matter of the present invention entails the use of β-hydroxy ketones of the general formula (I):

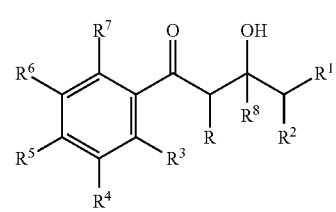

as scent precursors in washing and cleaning agents, wherein the radicals R, R1, R2, R3, R4, R5, R6, R7, R8 are defined as already indicated above.

Likewise, another subject matter of the present invention lies in the use of β-hydroxy ketones of general formula (I):

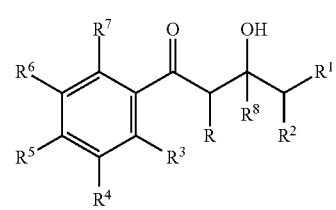

as scent precursors in cosmetic agents, wherein the radicals R, R1, R2, R3, R4, R5, R6, R7, R8 are defined as already indicated above.

It is particularly advantageous that the scent precursors according to the invention can also prolong the fragrancing effect of these fragrance substances in the presence of additional fragrance substances. Thus if the aforementioned use is directed at prolonging the fragrance effect of other fragrance substances which are also present in the washing and cleaning agent, cosmetic agent or air freshener, this is a preferred embodiment of the invention. Likewise another preferred embodiment of the invention is when the aforementioned use is directed at achieving a long-lasting fresh odor.

The use of the composition according to the invention to improve the yield of fragrance substance on textiles in particular is also the subject matter of the present invention.

As already described, softeners are preferred compositions in the sense of the invention. A softener according to the invention may usually contain a fabric softening component. It is most especially preferred if the fabric softening component is an alkylated quaternary ammonium compound, wherein at least one alkyl chain is interrupted by an ester group or an amido group.

The fabric softening component comprises, for example, quaternary ammonium compound such as monoalk(en)yltrimethylammonium compounds, dialk(en)yldimethylammonium compounds, mono-, di- or triesters of fatty acids with alkanolamines.

Suitable examples of quaternary ammonium compounds are shown, for example, in formulas (A-II) and (A-III):

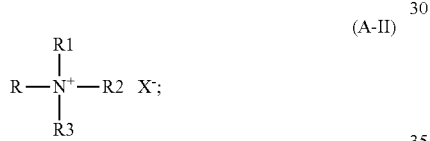

(A-II)

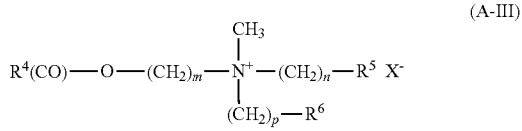

(A-III)

wherein in formula (A-II), R stands for an acyclic alkyl radical having 12 to 24 carbon atoms, R1 stands for a saturated $C_1$-$C_4$ alkyl or hydroxyalkyl radical, R2 and R3 are either the same R or R1 or stand for an aromatic radical. $X^-$ stands for a halide, methosulfate, methophosphate or phosphate ion and also mixtures of these. Examples of cationic compounds of formula (II) include monotallow trimethylammonium chloride, monostearyl trimethylammonium chloride, didecyldimethylammonium chloride, ditallow dimethylammonium chloride or dihexadecylammonium chloride.

Compounds of formulas (A-III) and (A-IV) are so-called ester quats. Ester quats are characterized by an excellent biodegradability. In formula (A-III) $R^4$ stands for aliphatic alk(en)yl radial having 12 to 22 carbon atoms with 0, 1, 2 or 3 double bonds and/or optionally with substituents; $R^5$ stands for H, OH or O(CO)$R^7$, $R^6$ stands independently of $R^5$ for H, OH or O(CO)$R^8$, wherein $R^7$ and $R^8$ independently of one another each stand for an aliphatic alk(en)yl radical having 12 to 22 carbon atoms with 0, 1, 2 or 3 double bonds; m, n and p may each have a value of 1, 2 or 3 independently of one another. $X^-$ may be a halide, methosulfate, methophosphate or phosphate ion as well as mixtures of these anions. Compounds in which $R^5$ stands for the group O(CO)$R^7$ are preferred. Especially preferred are compounds in which $R^5$ represents the group O(CO)$R^7$ and $R^4$ and $R^7$ are alk(en)yl radicals having 16 to 18 carbon atoms. In particular compounds in which $R^6$ also stands for OH are preferred. Examples of compounds of formula (A-II) include methyl-N-(2hydroxyethyl)-N,N-di(tallow acryloxyethyl)ammonium methosulfate, bis-(palmitoyloxyethyl)hydroxy-ethylmethylammonium methosulfate, 1,2-bis-[tallow acyloxy]-3-trimethylammoniumpropane chloride or methyl-N,N-bis-(stearoyloxyethyl)-N-(2-hydroxyethyl)ammonium methosulfate.

If quaternized compounds of the formula (A-III) are used having unsaturated alkyl chains, the acyl groups whose corresponding fatty acids have an iodine value between 1 and 100 preferably between 5 and 80 more preferably between 10 and 60 and in particular between 15 and 45 and having a cis/trans isomer ratio (in wt %) of more than 30:70, preferably greater than 50:50 and in particular the same as or greater than 60:40 are preferred. Conventional commercial examples include the methyl hydroxyalkyldialkyl-oxyalkylammonium methosulfate distributed by Stepan under the Stepantex® or the products from Cognis known by the brand name Dehyquart®, the products of Degussa known by the brand name Rewoquat® and/or the products from Kao known by the brand name Tetranyl®. Other preferred compounds include the diester quats of formula (A-IV) available by the names Rewoquat® W 222 LM and/or CR 3099.

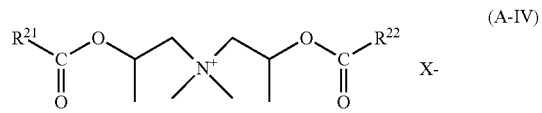

(A-IV)

$R^{21}$ and $R^{22}$ independently of one another each stands for an aliphatic radical with 12 to 22 carbon atoms with 0, 1, 2 or 3 double bonds.

Instead of the ester group O(CO)$R^{22}$, wherein $R^{22}$ stands for a long chain alk(en)yl radical, fabric softening compounds containing the following groups may also be used: RO(CO), N(CO)R or RN(CO), wherein of these groups, N(CO)R groups are preferred.

In addition, cationic polymers are also suitable fabric softening components. Polyquaternized components (e.g., Luviquat® Care from BASF) as well as cationic biopolymers based on chitin and derivatives thereof, for example, the polymer obtainable under the brand name Chitosan® (manufacturer Cognis) may also be used.

Particularly preferred fabric softening components are alkylated quaternary ammonium compounds, of which at least one alkyl chain is interrupted by an ester group and/or an amido group. Most especially preferred are N-methyl-N-(2-hydroxyethyl)-N,N-(ditallow acryloxyethyl)ammonium methosulfate or bis-(palmitoyloxyethyl)hydroxyethylmethylammonium methosulfate.

The composition according to the invention in the form of fabric softeners may also contain nonionic fabric softening components, such as in particular polyoxyalkylene glycerol alkanoates, polybutylenes, long-chain fatty acids, ethoxylated fatty acid ethanolamides, alkyl polyglucosides, in particular sorbitan mono-, di- and triesters and fatty acids of polycarboxylic acids.

In the fabric softener according to the invention, the fabric softening component is present in amounts of, for example, 0.1 to 80 wt %, usually 1 to 40 wt %, preferably 2 to 20 wt % in particular 3 to 15 wt % as the fabric softening component and the additional fragrance substance is advantageously present in amounts of 0.1 to 20 wt %, preferably 1 to 13 wt %, in particular 2 to 8 wt %, each based on the total amount of the agent according to the invention. The aforementioned fabric softening components may also be used in other compositions according to the invention, e.g., washing or cleaning agents, cosmetics, e.g., in the aforementioned quantities.

As an additional component, a composition according to the invention, e.g., a washing or cleaning agent, but in particular a fabric softener may optionally contain one or more nonionic surfactants, wherein such surfactants, which are usually also used in washing agents, may also be used here.

As optional nonionic surfactants, preferably alkoxylated, advantageously ethoxylated, in particular primary alcohols, preferably having 8 to 18 carbon atoms and an average of 1 to 12 mol ethylene oxide (EO) per mol alcohol may be used, in which the alcohol radical may be linear or preferably methyl-branched in position 2 and/or may contain linear and methyl-branched radicals in mixture such as those usually obtained in oxoalcohols radicals. In particular, however, alcohol ethoxylate having linear radicals of alcohols of native origin with 12 to 18 carbon atoms, for example, from coconut, palm, tallow fat or oleyl alcohol and an average of 2 to 8 EO per mol alcohol are preferred. The preferred ethoxylated alcohols include, for example, $C_{12-14}$ alcohols with 3 EO, 4 EO or 7 EO, $C_{9-11}$ alcohol with 7 EO, $C_{13-15}$ alcohols with 3 EO, 5 EO, 7 EO or 8 EO, $C_{12-18}$ alcohols with 3 EO, 5 EO or 7 EO and mixtures of these, such as mixtures of $C_{12-14}$ alcohol with 3 EO and $C_{12-18}$ alcohol with 7 EO. The specified degrees of ethoxylation are statistical averages, which may be an integer or a fraction for a specific product. Preferred alcohol ethoxylates have a narrow homolog distribution (narrow range ethoxylates, NRE). In addition to these nonionic surfactants, fatty alcohols having more than 12 EO may also be used. Examples include tallow fatty alcohol with 14 EO, 25 EO, 30 EO or 40 EO. Nonionic surfactants containing EO and PO groups together in the molecule may also be used according to the invention. Block copolymers with EO-PO block units and/or PO-EO block units may also be used but EO-PO-EO copolymers and/or PO-EO-PO copolymers may also be used. Mixed alkoxylated nonionic surfactants in which EO and PO units are not distributed by blocks but instead are distributed randomly may of course also be used. Such products are obtainable by the simultaneous action of ethylene oxide and propylene oxide on fatty alcohols.

Furthermore, alkyl glycosides of the general formula $RO(G)_x$ wherein R denotes a primary linear or methyl-branched aliphatic radical, in particular methyl-branched in position 2 and having 8 to 22 preferably 12 to 18 carbon atoms, and in which G is the symbol standing for a glucose unit having 5 or 6 carbon atoms, preferably glucose, may also be used as additional optional nonionic surfactants. The degree of oligomerization x, which indicates the distribution of monoglycosides and oligoglycosides, may be any number between 1 and 10, but x is preferably 1.2 to 1.4.

The nonionic surfactants may be present in the compositions according to the invention preferably in amounts of 0-30 wt %, e.g., in amounts >0.1 wt %. For example, it is possible that the compositions contain 2 to 30 wt %, preferably 7 to 20 wt %, and in particular 9 to 15 wt % nonionic surfactant, the wt % being based on the total composition in each case.

A composition according to the invention may optionally also contain anionic surfactant, e.g., in amounts of 0-30 wt %, preferably >0.1 wt %. For example, it is possible for the compositions to contain 2 to 30 wt %, preferably 7 to 20 wt %, and in particular 9 to 15 wt % anionic surfactant, the wt % being based on the total composition in each case.

For example, an anionic surfactant of the sulfonate and sulfate type may be used as the optional anionic surfactant. Surfactants of the sulfonate type preferably include $C_{9-13}$ alkyl benzene sulfonates, olefin sulfonates, i.e., mixtures of alkene and hydroxyalkane sulfonates as well as disulfonates, such as those obtained, for example, from $C_{12-18}$ monoolefins having terminal or internal double bonds by sulfonation with gaseous sulfur trioxide and subsequent alkaline or acidic hydrolysis of the sulfonation products. Preferred anionic surfactants are soaps in particular. Saturated and unsaturated fatty acid soaps such as the salts of lauric acid, myristic acid, palmitic acid, stearic acid, (hydrogenated) erucaic acid and behenic acid as well as in particular soap mixtures derived from natural fatty acids, for example, coconut, palm kernel, olive oil or tallow fatty acids are suitable.

The anionic surfactants including the soaps may be present in the form of their sodium, potassium or ammonium salts as well as soluble salts of organic bases such as mono-, di- or triethanolamine. The anionic surfactants are preferably present in the form of their sodium or potassium salts, in particular in the form of the sodium salts.

It is also preferable for the composition according to the invention in particular in the form of a washing or cleaning agent (e.g., textile or surface treatment agent) to additionally contain additional advantageous ingredients with which those skilled in the art are fundamentally familiar. The composition according to the invention, in particular in the form of a washing or cleaning agent (e.g., textile or a surface treatment agent) may contain additional ingredients which further improve the aesthetic properties of the agent and/or its technical properties in applications. Within the scope of the present invention, preferred compositions (in particular in the form of a washing or cleaning agent) additionally contain one or more substances from the group of builders, bleaching agents, bleach activators, enzymes, electrolytes, nonaqueous solvents, pH adjusting agents, perfume vehicles, fluorescent agents, coloring agents, hydrotropes, foam inhibitors, silicone oils, anti-redeposition agents, optical brighteners, graying inhibitors, flow preventers, antiwrinkle agents, dye transfer inhibitors, antimicrobial active ingredients, germicides, fungicides, antioxidants, preservatives, corrosion inhibitors, antistatics, bitter agents, ironing aids, phobicizing and impregnation agents, swelling agents and anti-slip agents, neutral filler salts and UV absorbers.

For example, silicates, aluminosilicates (in particular zeolites), carbonates, salts of organic dye and polycarboxylic acids as well as mixtures of these substances may be mentioned as builder substances, which may optionally be present in the compositions according to the invention (in particular washing or cleaning agents), e.g., in amounts >0.1 wt % (based on the total composition).

A composition according to the invention may optionally contain a thickener, e.g., in amounts >0.01 wt % (based on the total composition). This corresponds to a preferred embodiment of the invention. The thickener may be, for example, a polyacrylate thickener, xanthan gum, gellan gum, guar gum, alginate, carrageenan, carboxymethyl cellulose, bentonites, wellan gum, carob bean meal, agar, gum tragacanth, gum arabic, pectins, polyoses, starch, dextrins, gelatin and casein.

Water may be present in the liquid compositions according to the invention, preferably in amounts >5 wt %, e.g., in amounts of 10-95 wt %, preferably 20-80 wt %, in particular 30-70 wt %, the wt % being based on the total composition. Water may also be present in solid compositions according to the invention, but then naturally in a smaller amount accordingly, for example, in amounts of <5 wt % or e.g., <3 wt %.

Nonaqueous solvents which may optionally be used in the (preferably liquid) compositions according to the invention originate, for example, from the group of monovalent or polyvalent alcohols, alkanolamines or glycol ethers.

The viscosity of the compositions according to the invention, if they are liquid, may be measured with conventional standard methods (for example, Brookfield viscometer LVT-II at 20 rpm and 20° C., spindle 3) and is preferably 20 to 4000 mPas, but values between 40 and 2000 mPas are especially preferred. The viscosity of soft rinses is in particular preferably in the range of 40 to 1000 mPas.

To bring the pH of the composition according to the invention, if it is liquid, into the desired range, the use of pH adjusting agents may be indicated. All known acids and bases may be used here as long as their use is not contraindicated for ecological reasons or for technical reasons pertaining to the application and/or for reasons of consumer protection. The quantity of these adjusting agents usually does not exceed 7 wt % or preferably 5 wt % of the total formulation. The lower limit may be, for example, 0.1 wt %. The pH of the composition according to the invention, if it is liquid, is preferably between 1 and 6 and especially preferably between 1.5 and 3.5.

The agents and/or compositions according to the invention may be solid or liquid formulations, wherein the solid or liquid formulations, wherein the solid formulations may be present in the form of powders, granules, extrudates, in tab form, as a tablet or pressed and/or molten molded bodies. The liquid formulations may be solutions emulsions, dispersions, suspensions, microemulsions, gels or pastes.

The β-hydroxy ketones of general formula (I) used according to the invention:

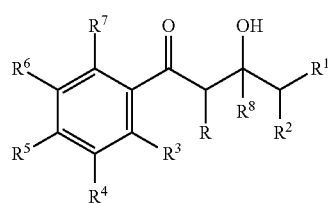

are accessible via an aldol reaction of corresponding compounds of formula (IV) such as in particular acetophenone derivatives or propiophenone derivatives:

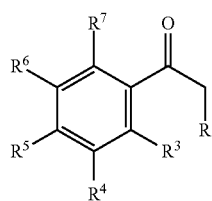

and carbonyl compounds of figure (V):

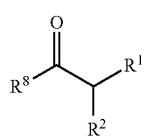

wherein the radicals R, R1, R2, R3, R4, R5, R6, R7, R8 are defined as indicated above in conjunction with formula (I). In particular they can be synthesized by the route of $TiCl_4$/$NBu_3$-induced aldol reactions (literature: Y. Tanabe et al., Tetrahedron 58 (2002), 8269-8280).

The β-hydroxy ketones of general formula (I) are preferably purified by crystallization, distillation and/or column chromatography.

EXAMPLE (a) Synthesis of (2R,3S)-3-hydroxy-2-methyl-1-phenyldecan-1-one

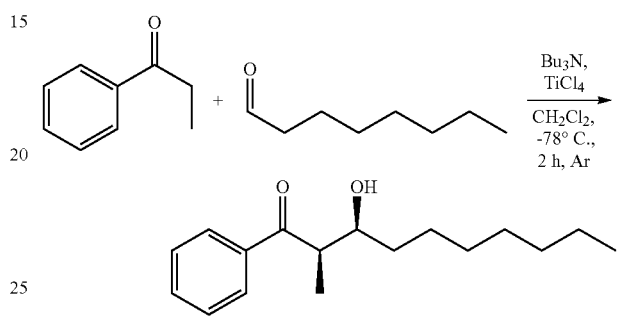

In a heated Schlenk flask flooded with argon 2.7 mL (20 mmol) propiophenone was placed in 40 mL absolute dichloromethane. This solution was cooled to −78° C. First 24 mL of a 1M titanium tetrachloride solution in dichloromethane was added to this solution and then 4.8 mL (28 mmol) tributylamine was added by drops with a syringe. After stirring for 30 minutes at −78° C., 3.8 mL (24 mmol) octanol was added. The reaction mixture was stirred for 2 more hours at −78° C. The reaction solution was quenched with 40 mL water and extracted twice with diethyl ether. The organic phase was washed with water, saturated NaCl solution and dried over $MgSO_4$. The filtrate was freed of solvent under reduced pressure. The raw product was purified by column chromatography (petroleum ether:ethyl acetate=95:5). Yield 80%. Analytical Data: Rf=0.3; Bp=175-180° C.; $^1$H-NMR (300 MHz, $CDCl_3$): δ=0.88 (3H, t, J=6.9 Hz), 1.25-1.58 (13H, m), 3.07 (s, 1H, O—H), 3.47 (1H, dq, J=2.8, 7.2 Hz), 4.03 (1H, m), 7.46-7.52 (2H, m), 7.53-7.62 (1H, m), 7.93-7.97 (2H, m). $^{13}$C-NMR (300 MHz, $CDCl_3$): 11.02, 14.10, 22.65, 26.11, 29.26, 29.59, 31.82, 34.33, 44.45, 71.34, 128.47, 128.77, 133.44, 135.92, 205.98.

(b) Exposure of (2R,3S)-3-hydroxy-2-methyl-1-phenyldecan-1-one (2R,3S)-3-Hydoxy-2-methyl-1-phenyldecan-1-one was dissolved in benzene. The reaction solution was exposed for 1 hour in a multilamp photoreactor (8 watt lamps (4×), the company Luxchem) with an emission maximum of λ=350 nm. The reaction was followed with the help of GCMS spectroscopy. After 60 minutes of exposure at the latest, almost complete conversion of (2R,3S)-3-hydroxy-2-methyl-1-phenyldecan-1-one to phenyl ethyl ketone and octanal was observed.

(c) Smell Test:

For the smell test, 0.2 mmol (2R,3S)-3-hydroxy-2-mthyl-1-phenyldecan-1-one was dissolved in 1 mL dipropylene glycol. A smell test strip was immersed 2 cm deep in the solution and then dried in the absence of light at 20° C. Two smell test strips were prepared in this way.

After successful drying, the first smell test strip was irradiated over the entire test period using a conventional fluorescent tube (according to DIN 5035 neutral white (nw); color temperature 3300 to 5500 K) and the fragrance intensity was determined at the respective times indicated.

The second odorant substance strip was stored in darkness.

The scent intensity was evaluated by three trained volunteers on a scale of 0 to 6, where 6 is the highest note and 0 stands for no perceptible scent.

Definition of the scaling:
6 unpleasantly strong
5 very strong
4 strong
3 intense
2 pleasant
1 perceptible
0 no longer perceptible The results of the smell test are presented in the following table, wherein the values indicated reflect the range of scent perception of the volunteer group.

|  | after 30 minutes | after 60 minutes | after 90 minutes |
|---|---|---|---|
| Odorant substance strip 1 | 0-1 fatty note | 2 fatty note | 2 fatty note |

The odorant substance strip 2 which was handled in darkness does not have a scent after 30, 60, 90 minutes and also not after several hours of storage (e.g., 17 hours) (corresponding value 0 according to the above scale).

However, it was found that the odorant substance strip 2 already produced a pleasant scent impression after only 60 minutes (corresponding to the value 2 according to the above scale, fatty scale) after first being stored in darkness for 17 hours and then irradiated as indicated above.

We claim:

1. A washing, cosmetic, or air freshener composition comprising from about 0.01 to about 5 wt %, based on the total amount of the composition, of at least one β-hydroxy ketone comprises structure (VI)

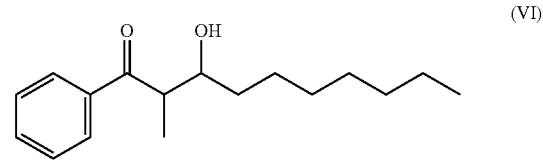 [SMILES: CCCCCCCC(O)C(C)C(=O)c1ccccc1]

(VI)

wherein the composition further comprises from about 0.01 to about 5 wt %, based on the total amount of the composition, of at least one additional fragrance substance selected from the group consisting of fragrance aldehydes and fragrance ketones; and wherein the composition further comprises at least one surfactant selected from the group consisting of anionic, cationic, nonionic, zwitterionic, and amphoteric surfactants, and mixtures thereof.

* * * * *